United States Patent [19]

Levins et al.

[11] 4,346,222
[45] Aug. 24, 1982

[54] 1,3,5,5-TETRANITROHEXAHYDROPYRIMIDINE (DNNC)

[75] Inventors: Donald A. Levins, San Jose; Clifford D. Bedford, Mountain View; Clifford L. Coon, Fremont, all of Calif.

[73] Assignee: SRI International, Menlo Park, Calif.

[21] Appl. No.: 212,816

[22] Filed: Dec. 4, 1980

[51] Int. Cl.³ ............................................ C07D 239/04
[52] U.S. Cl. ...................................... 544/322; 149/92
[58] Field of Search ........................................ 544/322

[56] References Cited

U.S. PATENT DOCUMENTS 3,000,890  9/1961  Frankel ................................. 544/322
3,041,337  1/1962  Frankel ................................. 544/322
3,923,804  12/1975  Sitzmann et al. .................... 544/322

OTHER PUBLICATIONS

Milton B. Frankel, Heterocyclic Polynitro Compounds, J. Org. Chem., 26, 4709, (1961).
R. G. Gafurov, et al., New Derivatives of 3,3,3-Trinitro-1-Aminopropane and Their Nitrolysis, Izx. aka, Nauk. SSSR, Sr. Khim., 6, 1366, (1973).
Arthur F. Farminer and Graham A. Webb, Nitration and Nitrosation Reactions of 7-Nitro-1,3,5-Triaza-Adamantane and Derivatives, J.C.S. Berkin I, 940 (1976).

Primary Examiner—Mary C. Lee
Assistant Examiner—James H. Turnipseed
Attorney, Agent, or Firm—Urban H. Faubion

[57] ABSTRACT

1,3,5,5-Tetranitrohexahydropyrimidine, termed DNNC for convenience, useful as an oxident in explosive and rocket propellant compositions. Said compound has the structure

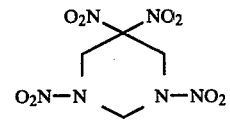

1 Claim, No Drawings

1,3,5,5-TETRANITROHEXAHYDROPYRIMIDINE (DNNC)

SPONSORSHIP

The invention described herein was made in course of work under Contract No. F04611-78-C-0051 from the Department of Defense.

BACKGROUND OF THE INVENTION

Prior Art

M. B. Frankel, J. Org. Chem., 26, 4709 (1961).
Reference shows the reaction of 2,2-dinitro-1,3-propanediol with polynitroaliphatic primary amines and formaldehyde to give 1,3-bis(3',3',3'-trinitropropyl) and 1,3-bis(3,3-dinitrobutyl)-5,5-dinitrohexahydropyrimidine.

R. G. Gafurov, S. I. Sviridov and L. T. Eremenko, Izv. Akad. Nauk. SSSR, Ser. Khim., 6, 1366 (1973).
Reference shows thorough investigation of the products of the reaction described in the previous reference as well as the nitration of 1,3-bis(3',3',3'-trinitropropyl)-5,5-dinitrohexahydropyrimidine to give 1,1,3,6,6-hexanitro-3-azaheptane.

A. F. Farminer and G. A. Webb, J.C.S. Perkin I, 940 (1976).
Reference describes the nitration of 7-nitro-1,3,5-triazaadamantane. Seven 1,3,5-trinitrohexahydropyrimidines, each with a different additional substituent at the 5-position were obtained.

Mention may also be made of two compounds which find widespread usage as rocket fuel oxidants. The first of these compounds, commonly termed HMX, is 1,3,5,7-tetranitro-1,3,5,7-octahydrotetrazocine. This compound has the structure

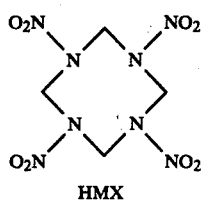

HMX

The other compound, commonly termed RDX, is 1,3,5-trinitro-1,3,5-hexahydrotriazine. This compound has the structure

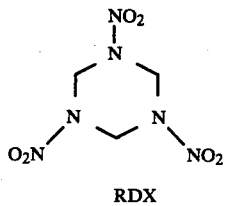

RDX

As compared to the DNNC compound of the present invention, the compounds of the prior art are relatively lean in oxygen in the sense of containing little if any oxygen over and above that required to burn the compound to CO and $H_2O$. In expressing the available oxygen value of a given oxidant compound, reference can be made to its "oxygen balance". This characteristic is determined by first calculating the number of oxygen atoms theoretically left in the compound after burning the same to CO, $H_2O$ and $N_2$ in the absence of any external oxygen source. The number so obtained is then divided by the molecular weight of the oxygen compound under test, with the value so obtained being multiplied by 1,000. Using this method all the prior art compounds mentioned above are found to have an oxygen balance equal to, or less than 0%, while DNNC has the relatively high oxygen balance of 6%.

THE INVENTION

The present invention rests on the discovery of the novel compound 1,3,5,5-tetranitrohexahydropyrimidine, termed DNNC for convenience. This compound has excellent utility as a rocket fuel oxidant. Thus, it has an oxygen balance of 6% coupled with very low impact sensitivity. That is to say, it requires a high impact force to cause the compound to detonate.

The method of preparation of the compound is given below first in "stick" form and then in a detailed fashion.

EXAMPLE

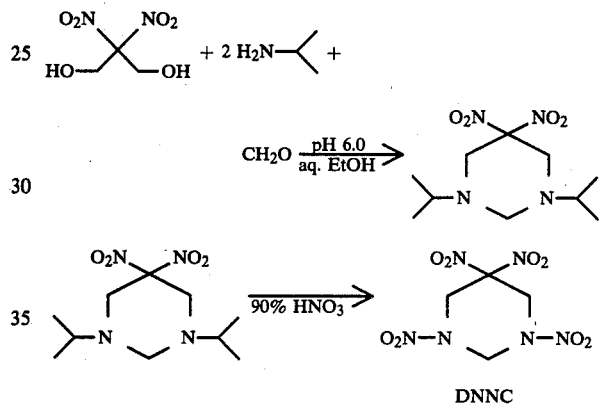

The intermediate, 1,3-diisopropyl-5,5-dinitrohexahydropyrimidine, was prepared by adding 5.9 g isopropylamine dropwise to a solution of 8.3 g 2,2-dinitro-1,3-propanediol and 3.75 ml of 37% aqueous formaldehyde in 50 ml 60% aqueous ethanol at 23° C.

The pH of the reaction mixture was maintained at 6.0 during the addition by the addition of concentrated HCl. The reaction mixture was stirred at room temperature for 45 minutes followed by extraction with methylene chloride. The methylene chloride extract was dried over $MgSO_4$ and flash evaporated, yielding 8.0 g of the desired intermediate as a faint yellow oil. Yield 61%, based on 2,2-dinitro-1,3-propanediol. DNNC was prepared by the addition of 0.5 g fresh 1,3-diisopropyl-5,5-dinitrohexahydropyrimidine in one portion to 10 ml 90% nitric acid. The temperature was maintained at 23° C. by a cold water bath. The mixture was stirred overnight at room temperature then poured into 30 ml ice. The aqueous reaction mixture was then filtered to remove a small quantity of precipitated DNNC. The filtrate was extracted with ether. The ether solution was washed with 5% NaOH followed by water, and then dried over $MgSO_4$. The dry ether extract was then flash evaporated yielding a white solid which was recrystallized from ethanol. Yield, 15% based on the starting hexahydropyrimidine.

DNNC is a crystalline solid whose chemical and physical properties are as follows:

| | |
|---|---|
| Molecular Formula: | C$_4$H$_6$N$_6$O$_8$ |
| Formula Weight: | 266.13 |
| Oxygen Balance: | 6.0% (balanced to CO, H$_2$O, N$_2$) |
| Appearance: | Colorless, transparent needles |
| Melting Point: | 151-4° C. |
| Decomposition Onset: | 188° C. (D.S.C.) |
| Density: | 1.82 (23° C.) |
| Heat of Formation: | 12.7 kcal/mole, 4.8 kcal/100 g (calc.) |
| Detonation Characteristics (Kamlet): | Pressure 340 kbar Velocity 8733 m/sec |
| Impact Sensitivity: | Technoproducts closed cup method, Data Bulletin 66830. |

-continued

| Compound | H$_{50\%}$, kg-cm* |
|---|---|
| DNNC | 3 pos. out of 12 at 300 |
| HMX | 164 |
| RDX | 136 |

*This test is performed by dropping a known weight from a known height on successive samples of DNNC until the drop height is established that causes 50% of the samples to detonate. H$_{50\%}$, kg-cm is the force in kg-cm required to detonate 50% of the samples tested. In the case of DNNC, at the test machine maximum of 300 kg-cm, only 3 out of 12 samples, or 25%, detonated.

What is claimed is:
1. 1,3,5,5-Tetranitrohexahydropyrimidine.

* * * * *